United States Patent [19]
Cassidy et al.

[11] 4,207,395
[45] Jun. 10, 1980

[54] PROCESS FOR DEACYLATING N-ACYL-6-SUBSTITUTED-2-[2-AMINOE-THYLTHIO]-1-CARBADETHIAPEN-2-EM-3-CARBOXYLIC ACIDS

[75] Inventors: Patrick J. Cassidy; Jean S. Kahan, both of Rahway, N.J.

[73] Assignee: Merck & Co., Inc., Rahway, N.J.

[21] Appl. No.: 956,951

[22] Filed: Nov. 2, 1978

[51] Int. Cl.$^2$ .............................................. C12P 17/18
[52] U.S. Cl. .................................................... 435/119
[58] Field of Search ..................... 195/29, 36 P, 36 C; 435/119

[56] References Cited

U.S. PATENT DOCUMENTS 4,135,978  1/1979  Kahan et al. ........................ 195/29

*Primary Examiner*—Raymond N. Jones
*Assistant Examiner*—Robert J. Warden
*Attorney, Agent, or Firm*—Frank M. Mahon; Julian S. Levitt; James A. Arno

[57] ABSTRACT

Disclosed is a process for enzymatically cleaving the acyl group from N-acyl-6-substituted-2-substituted-1-carbadethiapen-2-em-3-carboxylic acids. The acylated substrate and the deacylated product are antibiotics.

6 Claims, No Drawings

PROCESS FOR DEACYLATING N-ACYL-6-SUBSTITUTED-2-[2-AMINOETHYLTHIO]-1-CARBADETHIAPEN-2-EM-3-CARBOXYLIC ACIDS

BACKGROUND OF THE INVENTION

This invention relates to an enzymatic process for deacylating N-acyl-6-substituted-2-substituted-1-carbadethiapen-2-em-3-carboxylic acids (I); such acylated species (I) and corresponding deacylated forms are antibiotics:

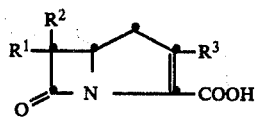

wherein $R^1$ and $R^2$ are, inter alia, independently selected from the group consisting of hydrogen, substituted and unsubstituted alkyl, aralkyl, aryl, alkenyl and the like and $R^3$ is a similarly broadly defined radical which is characterized for purposes of this process by having an amino group which bears an acyl group $R^°$. Many of such compounds I are known and available to the art. See for example, Belgium Patent No. 860,962 (filed Nov. 18, 1977). The balance of such compounds I are disclosed and claimed in co-pending, commonly assigned U.S. Patent Application Ser. No. 933,681 (filed Aug. 17, 1978) which is incorporated herein by reference.

A sub-cateogry under generic structure I includes the 6-ethyl species 1:

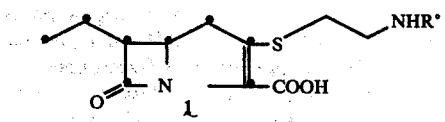

$R^°$ is acyl as defined above.

Species 1 is known ($R^°$ =acetyl) and available to the art; see the *Journal of Antibiotics;* Volume 31, No. 5 pages 480–482 (May 1978); such species and deacylated species are disclosed and claimed in co-pending, commonly assigned U.S. Patent Applications Ser. Nos. 933,681 (filed Aug. 17, 1978) and 861,230 (filed Dec. 16, 1977 which are incorporated herein by reference. Substrate species (genus, I, above), such as 1 (above), which are isolated from fermentation broths commonly have acetyl as the acyl group ($R^°$); whereas those obtained semi-synthetically or by total synthesis are not limited to acetyl, or any other lower alkanoyl, and may have any value for the acyl group $R^°$. It is desirable to have a process for obtaining the free amino (deacylated) species, for such species usually demonstrate enhanced antibiotic activity. Also, the deacylated antibiotic may also be regarded as an intermediate for subsequent derivatization of the amino group; such derivatization processes, however, are not embraced by the present invention. As a class, whether derived from animal tissues or micro-organism, the amido acylases are effective enzymes to achieve the desired transformation. Members of the amidoacylase enzyme genus which effect the desired cleavage are given below.

DETAILED DESCRIPTION OF THE INVENTION

Susceptible N-acyl substrates of interest embraced by I, above, include those wherein $R^1$ and $R^2$ are independently selected from the group consisting of hydrogen, substituted and unsubstituted: alkyl and alkenyl having from 1–6 carbon atoms, aralkyl such as alkylphenyl, and aryl such as phenyl wherein the substituent or substituents are selected from hydroxyl, amino and carboxyl; and wherein $R^3$ is selected from:

—S—(R)—NHR°

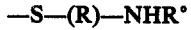
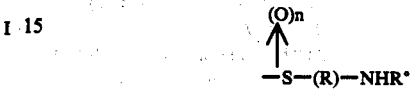

—O—(R)—NHR°, and

—R—NHR°; wherein R is lower alkyl or alkenyl having from 1–6 carbon atoms, phenyl or phenyl-loweraralkyl; n is 1 or 2; and R° is acyl.

The term, "acyl" is by definition inclusive of the aliphatic and aromatic carboxylic acids including derivatives and analogues thereof. For purposes of this invention the term "acyl" and its definition is the same as that found in co-pending, commonly assigned U.S. Patent Application Ser. No. 861,247 (filed Dec. 16, 1977) which is directed to N-acyl derivatives of thienamycin and which is incorporated herein by reference. Representative values of such acyl radicals, R°, are indicated below.

For example, the acyl radical can be substituted or unsubstituted: aliphatic, aromatic, heterocyclic, araliphatic or heterocyclylaliphatic carboxylic acid radical, a substituted or unsubstituted: carbamyl radical or a carbothioic acid radical. One group of acyl radicals can be represented by the general formula:

wherein X is O or S and R" represents hydrogen, straight or branched chain alkyl group containing from 1–10 carbon atoms, aryloxy, having 6–10 carbon atoms, alkylthio, and arylthio having from 6–10 carbon atoms. Such above-listed groups can be unsubstituted or can be substituted by radicals such as OH, SH, SR (R is lower-alkyl or aryl such as phenyl), alkyl or alkoxy having 1 to 6 carbon atoms, halo, such as Cl, Br, F and I, cyano, carboxy, sulfamino, carbamoyl, sulfonyl, azido, amino, substituted amino such as alkylamino including quaternary ammonium wherein the alkyl group comprises 1–6 carbon atoms, haloalkyl such as trifluoromethyl, carboxyalkyl, carbamoylalkyl, N-substituted carbamoylalkyl, wherein the alkyl moiety of the foregoing four radicals comprises 1 to about 6 carbon atoms, amidino, guanidino, N-substituted guanidino, guanidino lower alkyl and the like. Representative examples of such acyl groups that might be mentioned are those wherein R" is hydrogen, methyl, benzyl phenoxymethylene, p-hydroxybenzyl, n-amyl, n-heptyl, 3- or 4-nitrobenzyl, phenethyl, β,β-diphenylethyl, methyldiphenylmethyl, triphenylmethyl, 2-methoxyphenyl, 2,6-dimethoxyphenyl, 2,4,6-trimethoxyphenyl, D-4-N-benzoylamino-4-carboxy-n-butyl, p-aminobenzyl, o-aminobenzyl, m-aminobenzyl, p-dimethylaminobenzyl, 2-ethoxy-1- naphthyl, 4-guanidinomethylphenyl, 4-guanidinomethylbenzyl, 4-guanidinobenzyl, 4-guanidinophenyl, 2,6-dimethoxy-4-guanidino, o-sulfobenzyl, p-carboxymethylbenzyl, p-carbomoylmethylbenzyl, m-fluorobenzyl, m-bromobenzyl, p-chlorobenzyl, p-methoxybenzyl, 1-naphthylmethyl, 2-phenylvinyl, 2-phenylethynyl, phenyl, o-methoxyphenyl, o-chlorophenyl, o-phenylphenyl, and aminomethylbenzyl.

Preferred deacetylation enzymes include: N-acyl amidohydrolases which may be isolated from animal tissues (J. Greenstein and M. Winitz, Chemistry of the Amino Acids; Wiley, N.Y., 1961; p. 1753) and particularly from hog kidneys (S. Birnbaumin, *Methods in Enzymology Vol.* 2. Academic Press, N.Y., 1955). Deacylating enzymes have also been isolated from bacterial species such as Protaminobacter ruber, Alcaligenes faecalis MB3772, Pseudomonas (several species), as well as fungi such as Aspergillus oryzae and other microorganisms.

Relative to the organism designated MB3772 (above), which is the culture designation of Merck & Co., Inc., Rahway, New Jersey, a culture has been placed on irrevocable, permanent deposit with the culture collection of the AMERICAN TYPE CULTURE COLLECTION, 12301 Parklawn Drive, Rockville, Maryland 20852 and is available to the public under assigned Accession Number 31444.

Deacylation may also be accomplished by the penicillin amidohydrolase (EC 3.5.1.11) obtained from several bacterial species. However, the relative activities of these enzymes on the several substrates of this invention will not in general be identical, and in particular the penicillin amidohydrolase will be more active in cleaving aromatic acyls; whereas the animal tissue acylases will more readily hydrolyse short-chain acyl groups such as acetyl, chloro-acetyl, and the like.

In general, the enzymes of this invention will be most suitable after purification and concentration, so as to obtain the best yield of product. Purification procedures for these enzymes may be any of the purification procedures widely used and well known to those skilled in the art, such as salt or solvent fractionation, gel filtration, ion-exchange column chromatography, affinity chromatography, hydroxyapatite chromatography, protamine or streptomycin precipitation, metal ion precipitation, aluminum or other gel absorption, pH precipitation, heat treatment, phase distribution, gel or free-flow electrophosesis, high-speed centrifugation, isolectric focusing, and the like. To assist in purification of these enzymes, systems to assay deacetylating activity may include: radioactive substrates, such as ($^3$H-acetyl)-thienamycin, prepared by treating thienamycin with $^3$H-acetic anhydride in dimethylformamide. In this regard and for purposes of general discussion, reference is made to co-pending, commonly assigned U.S. Patent Application Ser. No. 861,247 (filed Dec. 16, 1977), which is incorporated herein by reference.

Generally, the deacylation is accomplished by contacting the substrate I(above) with an enzyme capable of accomplishing the deacylation and providing the free amino species. This transformation normally occurs in solution phase wherein the substrate and the deacylating enzymes are contacted; the enzyme may be free or fixed on a bed over which the substrate in solution is passed. Preferred deacylation enzymes include those mentioned above and include those isolated from hog kidney, Protaminobacter ruber NRRL B 8143 and other bacterial species. Typically the deacylation is accomplished on solutions of substrate in an aqueous medium having a pH of from 7.0 to 8.0 at a temperature of from 23° C. to 37° C.; wherein the concentration of substrate ranges from $10^{-4}$ to $10^{-1}$ molar and the deacylating enzyme is present in a ratio of from 1:1 to 1000:1 (substrate: enzyme). The following Examples representatively illustrate the enzymatic deacylation:

EXAMPLE 1

Process for deacylation of N-acetyl-6-ethyl-2-[2-aminoethylthio]-1-carbadethiapen-2-em-3-carboxylic acid

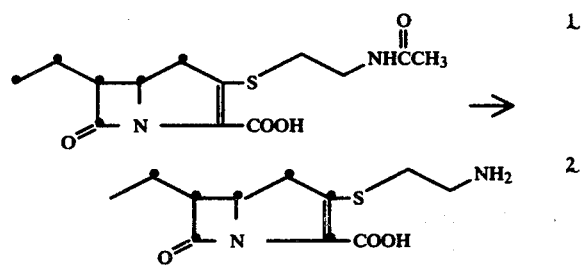

Step A

Preparation of Enzyme

Epithienamycin deacetylase I from hog kidneys is isolated by the following procedure. Frozen hog kidneys (200 g) are thawed overnight in a refrigerator, and homogenized with an equal weight of 0.05 M morpholino propylsulfonate (MOPS) buffer at pH 7.6 in a blender. Two additional portions of MOPS buffer equal to the first are added, and the homogenate is centrifuged. The supernatant is fractionated by addition of solid ammonium sulfate, and the fraction precipitating between 45% and 90% saturation is re-suspended in a minimum volume of MOPS buffer. After dialysis overnight into MOPS buffer, the sample is fractionated on a Sephadex G-100 column, and the lower molecular weight fractions of highest specific activity are pooled. (As mentioned above, specific activity is judged by using a radioactive substrate, specifically N-(H$^3$-acetyl)-thienamycin.) The pooled fractions are put on a column of DEAE-cellulose (CL$^-$) and eluted with a gradient of 0 to 0.50 M NaCl containing 0.02 M Tris-HCl buffer, pH 7.1. The fractions of highest specific activity are pooled and concentrated in an Amicon pressure cell using a UM-10 membrane. The concentrate is dialyzed against 0.01 M potassium phosphate buffer, pH 7.15, diluted with an equal volume of distilled water, and further chromatographed on a hydroxyapatite column using a gradient of 0.001 M to 0.50 M potassium phosphate, pH 6.8. The fractions of highest specific activity are pooled, concentrated in a pressure cell as above, and dialysed against 0.05 M MOPS, pH 7.6.

Step B, Enzymatic Deacylation

To a 0.2 ml solution of N-acetylaminohydrolase from Step A, (55 mg/ml) in 0.05 M morpholinopropyl sulfate (MOPS) buffer at pH 7.6, compound 1 (2 mg) is added. The solution is incubated at 28° C. Periodic tests are performed to monitor the integrity of the nuclear ring structure of the antibiotic as follows: a 5 μl portion of the reaction mix is added to 0.495 μl of 0.05 M potassium phosphate, pH 7.4 in an ultraviolet absorption cuvette. The absorbance at 295 nm is measured, and then 5 μl of 1 N hydroxylamine hydrochloride is added, and the decrease in absorbance is observed. When the absorbance at 295 reaches a minimum (10–30 minutes), the value is noted and the value after hydroxylamine treatment is subtracted from the value before addition of hydroxylamine to obtain the "Hydroxylamine Extinction" value. When the hydroxylamine extinction of reaction samples reaches one-half of the initial value, (i.e., the value immediately after addition of the compound 1), the reaction is terminated by addition of 1 ml deionized water, and chilling in ice. The pH of the solution is carefully adjusted to 8.0 by addition of 0.1 M NaOH, and the solution is then passed over a bed of Bio-Rad AG-1×2 (Cl-) (200–400 mesh) dimensions 1.5 cm×17 cm. The sample is eluted with deionized water and fractions of 3 ml are collected. Fractions with U.V. maximum absorbance at 295 nm are pooled and lyophilized to provide 2.

Following the procedure as described above except substituting for the acylase of Example 1 an equivalent amount of an amido hydrolase enzyme isolated from *Protaminobacter ruber*, or *Alcaligenes faecalis*, respectively, there is obtained equivalent deacylation and compound 2 is recovered.

Following the procedure of Example 1 except substituting an equivalent amount of the following substrates there is obtained the corresponding deacylated species:

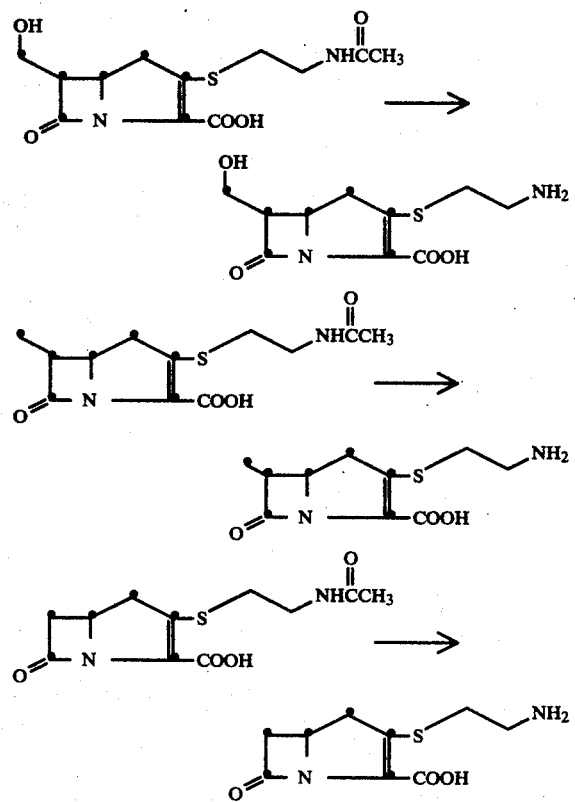

What is claimed is:
1. A process for preparing a compound having the structure:

wherein $R^1$ and $R^2$ are independently selected from the group consisting of hydrogen; substituted and unsubstituted: alkyl having 1-6 carbon atoms; phenyl and phenylalkyl wherein the substituent is selected from hydroxyl, amino, and carboxyl; $R^3$-$NH_2$ is alkylamino having 1-6 carbon atoms, phenylamino, phenylalkylamino, thioalkylamino, and alkylphenylalkylamino (each alkyl having 1-6 carbon atoms), which comprises contacting the corresponding N-acyl species having the structure:

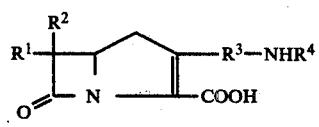

wherein $R^4$ is acyl, with an deacylating enzyme isolated from *Alcaligenes faecalis* ATCC 31444 capable of cleaving $R^4$; when $R^2/R^1$ is H and $R^1/R^2$ is 1-hydroxyethyl, —$R^3NHR^4$ is not $$-SCH_2CH_2NH\overset{O}{\overset{\|}{C}}CH_3.$$

2. A process according to claim 1 wherein $R^4$ is acetyl.

3. A process according to claim 2 for preparing a compound having the structure:

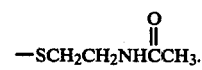

4. A process according to claim 2 for preparing a compound having the structure:

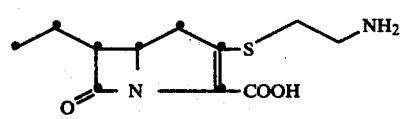

5. A process according to claim 2 for preparing a compound having the structure:

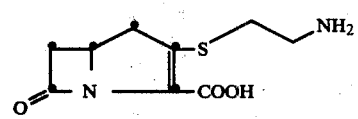

6. A process according to claim 2 for preparing a compound having the structure:

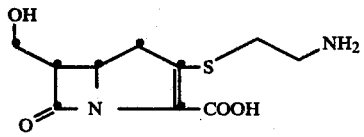

* * * * *